(12) United States Patent  
Wang

(10) Patent No.: US 9,700,734 B2  
(45) Date of Patent: Jul. 11, 2017

(54) ELECTROMAGNETIC THERAPY APPARATUS AND AUXILIARY PHYSIOTHERAPY LIQUID THEREOF

(75) Inventor: Hong Wang, Zibo (CN)

(73) Assignee: SHANDONG CHAO RUI SHI MEDICAL TECHNOLOGY CO., LTD, Zibo, Shandong (CN)

( * ) Notice: Subject to any disclaimer, the term of this patent is extended or adjusted under 35 U.S.C. 154(b) by 380 days.

(21) Appl. No.: 14/117,809

(22) PCT Filed: Jun. 12, 2012

(86) PCT No.: PCT/CN2012/000801  
§ 371 (c)(1),  
(2), (4) Date: Nov. 14, 2013

(87) PCT Pub. No.: WO2013/075391  
PCT Pub. Date: May 30, 2013

(65) Prior Publication Data  
US 2014/0309480 A1    Oct. 16, 2014

(30) Foreign Application Priority Data

Nov. 22, 2011 (CN) .......................... 2011 1 0371955

(51) Int. Cl.  
*A61N 2/12* (2006.01)  
*A61N 2/00* (2006.01)  
(Continued)

(52) U.S. Cl.  
CPC ........... *A61N 2/12* (2013.01); *A61H 15/0078* (2013.01); *A61H 15/02* (2013.01); *A61H 33/04* (2013.01);  
(Continued)

(58) Field of Classification Search  
CPC . A61N 2/00; A61N 2/12; A61N 2/002; A61N 2/02; A61K 36/13; A61K 36/237; A61K 36/286; A61K 36/41; A61K 2300/00; A61H 15/02; A61H 2203/0456; A61H 2201/5007; A61H 2201/5005;  
(Continued)

(56) References Cited

U.S. PATENT DOCUMENTS 5,667,469 A * 9/1997 Zhang ...................... A61N 2/12  
600/9

* cited by examiner

*Primary Examiner* — Christine H Matthews  
*Assistant Examiner* — Joshua D Lannu

(57) ABSTRACT

An electromagnetic therapy apparatus includes: upper magnetic heads mounted on a frame; lower magnetic heads mounted in a treatment bed, wherein each of the lower magnetic heads is connected to a rotary power supplier and is driven to rotate individually thereby, the lower magnetic heads drive the upper magnetic heads to rotate by magnetic force coupling; therapy clothes provided on a treatment bed and connected to a physiotherapy liquid collection tank through a circulation pump; self-heating tourmaline slices or metal clamps mounted in the therapy clothes; and a high-frequency heating induction coil mounted in the treatment bed and connected to a high-frequency power supplier. Auxiliary physiotherapy liquid includes: basic liquid; and a traditional Chinese medicine additive. By applying a magnetic principle of Western medicine on human bodies, anti-cancer and blood-thinning effects can be achieved. With high-speed metabolism, utilizing the traditional Chinese medicine can accelerate a recovery process.

17 Claims, 16 Drawing Sheets

(51) Int. Cl.
*A61H 15/02* (2006.01)
*A61K 36/13* (2006.01)
*A61K 36/237* (2006.01)
*A61K 36/286* (2006.01)
*A61K 36/41* (2006.01)
*A61N 2/02* (2006.01)
*A61H 15/00* (2006.01)
*A61H 33/04* (2006.01)
*A61H 39/06* (2006.01)

(52) U.S. Cl.
CPC .............. *A61H 39/06* (2013.01); *A61K 36/13* (2013.01); *A61K 36/237* (2013.01); *A61K 36/286* (2013.01); *A61K 36/41* (2013.01); *A61N 2/00* (2013.01); *A61N 2/002* (2013.01); *A61N 2/02* (2013.01); A61H 2015/0014 (2013.01); A61H 2033/048 (2013.01); A61H 2201/0111 (2013.01); A61H 2201/0207 (2013.01); A61H 2201/0214 (2013.01); A61H 2201/0221 (2013.01); A61H 2201/10 (2013.01); A61H 2201/105 (2013.01); A61H 2201/1654 (2013.01); A61H 2201/5005 (2013.01); A61H 2201/5007 (2013.01); A61H 2203/0456 (2013.01)

(58) Field of Classification Search
CPC ...... A61H 2201/1654; A61H 2201/105; A61H 2201/10; A61H 2201/0221; A61H 39/06; A61H 2201/0111; A61H 15/0078; A61H 33/04; A61H 2015/0014; A61H 2033/048; A61H 2201/0207; A61H 2201/0214
See application file for complete search history.

ELECTROMAGNETIC THERAPY APPARATUS AND AUXILIARY PHYSIOTHERAPY LIQUID THEREOF

CROSS REFERENCE OF RELATED APPLICATION

This is a U.S. National Stage under 35 U.S.C 371 of the International Application PCT/CN2012/000801, filed Jun. 12, 2012, which claims priority under 35 U.S.C. 119(a-d) to CN 201110371955.4, filed Nov. 22, 2011.

BACKGROUND OF THE PRESENT INVENTION

Field of Invention

The present invention relates to a field of medical instruments and auxiliary physiotherapy liquid thereof, and more particularly to an electromagnetic therapy apparatus and auxiliary physiotherapy liquid thereof.

Description of Related Arts

China is the first country to discover magnet 2000 years ago, the Chinese ancestors had found and applied magnetic principles on many aspects of life, especially on the medical field. The therapeutic effect of magnet is recorded in *Shen Nong's Herbal Classic* and *Compendium of Materia Medica* in detail. With the development of modern medicine, magnetic therapy has been a key study target in the world medical frontier.

Because of various magnetic material classifications, the application fields and scopes are not the same, wherein researches of gyromagnetic materials are the most notable. It is proved by the experiments that the magnetic microwave applied on the human body can change the normal movement state of a moving electric charge, which is called field force effect. Gyromagnetic materials emit magnetic waves. And the magnetic waves go into the human body for the purpose of diagnosis and treatment of diseases. In certain conditions, the magnetic waves can kill cancer cells.

According to *Science and Technology Daily* of Jun. 9, 2011, the latest research results showed that: blood viscosity of human can be reduced by the magnetic field. If the blood viscosity is too high, blood pressure will be increased, blood vessels will be damaged and the risk of heart attack will be increased. According to the report of the phys.org in June 8 (Beijing time), physicists of the U.S. Temple University recently discovered that magnetic field can reduce the blood viscosity of human, whose research paper has been published in a recent *Physical Review E*.

Currently, the most widely used medical method for diluting blood is utilizing drugs such as aspirin. However, these drugs may have side effects. Professor Rongjia Tao of the Temple University, who invented a method for reducing engine or pipe oil viscosity by utilizing electric or magnetic fields, extends the method to the control of blood viscosity. And after a lot of testing on blood samples, it has been proved that blood in the human circulatory system can be diluted by utilizing the magnetic field.

The principle of the magnetic field for reducing blood viscosity is as follows. Because the red cells comprise iron, applying a magnetic field can polarized the red cells in such a manner that the red cells are connected to each other in a short-chain and streamline motion form. Because the short chains are larger than a single blood cell, the friction with the vessel wall will be reduced when the short chains flow down towards the center. Therefore, the connection effect reduces the blood viscosity, and helps the blood to flow more smoothly. If a 1.3 T magnetic field is applied on the blood for about 1 min, blood viscosity will be reduced by 20%~30%, wherein the magnetic field strength is equivalent to the magnetic field strength of a MRI system. When the magnetic field is removed, the blood viscosity will slowly return to an original state, but the process will last for a few hours. "By choosing a suitable magnetic field strength and pulse time, we can control the size of red cell short chain, thereby controlling the blood viscosity. Magnetorheological provides an effective way for controlling the blood viscosity in a controllable range." Rongjia Tao explained. And this method is not only safe, but also repeatable. By applying magnetic field many times, the blood viscosity can be reduced while the normal function of the red cells is not affected.

Therefore, curing cancer and other incurable diseases or reducing blood viscosity with magnetic theory has become a new development direction of medicine. Compared with conventional surgery or chemotherapy treatments, the magnetic method not only reduces the cost, but also greatly reduces pain of patients, which is conducive to the cooperation and interaction of doctors and patients and has made remarkable achievements. However, because of medical application of magnetic technology is still a high-end interdisciplinary subject, there are few successful and effective magnetic therapy apparatus in the world.

With the development of times, the application of magnetic field in the medical field has got a more complete theoretical basis. The applicant has been devoted to the development of magnetic medicine and magnetic therapy apparatus for many years. And a variety of magnetic therapy apparatuses have been clinically applied. Therefore, a lot of valuable research and development information and experiences are obtained. The electromagnetic therapy apparatus according to the present invention is different from the conventional therapy apparatuses in that: the apparatus combines the latest research results of the magnetic medicine with essence methods of traditional Chinese medicine of physiotherapy, that is to say, the apparatus utilizes the magnetic field for physiotherapy with the help of Chinese medicine and acupuncture stimulation. Furthermore, with the help of electromagnetic heating principle, the effect is maximized and a variety of effects are combined, which fills the gap of traditional Chinese medicine magnetic therapy apparatus in the world.

SUMMARY OF THE PRESENT INVENTION

An object of the present invention is to provide an electromagnetic therapy apparatus and auxiliary physiotherapy liquid thereof, which have both a treatment effect and a care effect.

Accordingly, in order to accomplish the above object, the present invention provides an electromagnetic therapy apparatus, comprising:

a frame;

a treatment bed;

a plurality of upper magnetic heads mounted on the frame by bearings;

a plurality of lower magnetic heads mounted in the treatment bed, wherein each of the lower magnetic heads is connected to a rotary power supplier and is driven to rotate individually by the rotary power supplier; vertical mounting positions of the upper magnetic heads are respectively corresponding and opposite to vertical mounting positions of the lower magnetic heads; the rotary power suppliers drive the lower magnetic heads to rotate in such a manner that the lower magnetic heads drive the upper magnetic heads to rotate by magnetic force coupling; and therapy clothes provided on the treatment bed, wherein a waterproof sealing bars are provided on openings of the therapy clothes; the therapy clothes are connected to a physiotherapy liquid collection tank through a circulation pump; padding is provided in the therapy clothes, and one or more self-heating tourmaline slices or metal clamps are mounted between the therapy clothes and the padding.

Preferably, a high-frequency heating induction coil connected to a high-frequency power supplier is mounted in the treatment bed.

Preferably, the upper and lower magnetic heads are electromagnetic heads, a cooling device is provided around the electromagnetic heads; an induction electromotive force of an electromagnetic wave generated by the electromagnetic heads is 500~1000 mv with a frequency of 8~20 Hz; a plurality of electromagnetic blocks are spliced for forming the upper and lower magnetic heads, and gaps exist between the electromagnetic blocks.

Preferably, the upper and lower magnetic heads are permanent magnetic heads; a plurality of permanent magnetic blocks are spliced for forming the upper and lower magnetic heads, and gaps exist between the permanent magnetic blocks.

Preferably, static magnetic field strength of the upper and lower magnetic heads is 5000~8500 Gs.

Preferably, a rotation speed of the lower magnetic head is 50~600 rpm, a distance between the upper and lower magnetic heads is 200~400 mm.

Preferably, the upper and lower magnetic heads are disc-shaped, a ratio of a center distance between the magnetic heads and a diameter of the magnetic head is 1.2:1.

Preferably, the self-heating tourmaline slices or metal clamps are provided between the therapy clothes and the padding according to acupuncture points, cambered salient points are provided on the self-heating tourmaline slices or metal clamps.

Preferably, the therapy clothes are in a sleeping bag form or a split form.

Preferably, the therapy clothes in the split form comprise:
a head cover with ear, nose and mouth openings;
a body cover; and
limb covers;
wherein waterproof sealing bars are provided on the openings of the head, body and limb covers, and the head, body and limb covers are respectively connected to the physiotherapy liquid collection tank.

Preferably, a plurality of tourmaline slices or halite slices are provided on a top surface of the treatment bed.

Preferably, a plurality of emulsion rollers are provided on the treatment bed, and the emulsion rollers are mounted below a neck bend, a waist bend, leg bends and/or foot bends of the therapy clothes; the emulsion rollers are respectively connected to micro motors, and the micro motors drive the emulsion rollers to rotate individually.

Preferably, radial protrusions are provided on the emulsion roller, a top of the radial protrusion is inlaid with a halite grain; a metal heating mandrel is mounted in the emulsion roller; after the high-frequency power supplier provides a high-frequency alternating current for the high-frequency heating induction coil, the metal clamps and the metal heating mandrels generate heat at the same time.

Preferably, the frame comprises:
an upright post;
a lifting arm;
a lifter; and
a upper magnetic head holder;
wherein the lifting arm is inserted in the upright post and is driven to go up and down by the lifter; the upper magnetic head holder is connected to the lifting arm, the upper magnetic heads are mounted on the upper magnetic head holder.

Preferably, a heater is provided in the physiotherapy liquid collection tank and is connected to a temperature controller.

Preferably, the electromagnetic therapy apparatus further comprises: a computer control system, wherein the computer control system is connected to and controls the rotary power supplier, the circulation pump, the micro motors, the lifter and the temperature controller.

The present invention also provides auxiliary physiotherapy liquid of the electromagnetic therapy apparatus, comprising:
basic liquid; and
a traditional Chinese medicine additive;
wherein the basic liquid comprises:
glycerol; and
olive oil;
wherein a ratio of the glycerol and the olive oil is 1:1~1:3.

Preferably, the traditional Chinese medicine additive is selected from the group consisting of Chinese *angelica, safflower, Notopterygium, rattan Panax, yew, Agastache* and *sarmentosum*; a ratio of the basic liquid and the traditional Chinese medicine additive is 10:1~10:1.5.

Therefore, the present invention has advantages as follows.

A) When the upper and lower magnetic heads are the electromagnetic heads, the cooling device is provided around the electromagnetic heads. The induction electromotive force of the electromagnetic wave generated by the electromagnetic heads is 500~1000 mv with a frequency of 8~20 Hz. When the upper and lower magnetic heads are the permanent magnetic heads, a dynamic magnetic field with suitable waveform, strength and frequency is generated by controlling distances between the magnetic blocks, rotation speeds, phase difference of the upper and lower magnetic heads, etc.

The dynamic magnetic field of a pair of the magnetic heads can provide:
(a) chest treatments for breast and respiratory system;
(b) abdomen treatments for digestive system, urinary system and reproductive system; and
(c) leg treatments.

The dynamic magnetic field of two pair of the magnetic heads can provide:
(a) chest and abdomen treatments at the same time for multi-lesions; and
(b) abdomen and leg treatments at the same time for multi-lesions.

The dynamic magnetic field of three pair of the magnetic heads can provide: chest, abdomen and leg treatments at the same time for increasing treatment efficiency for systemic diseases.

When a plurality of the upper and lower magnetic heads are arranged in a matrix form and are activated in sequence, a blood viscous region of a patient spread to tributaries for relieving blood viscosity, thrombus disease, etc.

B) The therapy clothes are provided on the treatment bed, and the waterproof sealing bars are provided on the openings of the therapy clothes. After putting on the therapy clothes, the patient seals the openings by pressing the waterproof sealing bars in such a manner that the physiotherapy liquid is prevented from leakage. The physiotherapy liquid is stored in the physiotherapy liquid collection tank. The therapy clothes are connected to the physiotherapy liquid collection tank through the circulation pump. The physiotherapy liquid forms a uniform layered structure for covering the whole body and can flow circularly. When blood circulation and metabolism are accelerated by the magnetic field, the physiotherapy liquid can be absorbed easily and effects thereof can directly affect diseased portions for maximizing treatment effects.

C) The self-heating tourmaline slices or metal clamps are provided between the therapy clothes and the padding according to the acupuncture points. The cambered salient points are provided on the self-heating tourmaline slices or metal clamps for pressing and stimulating the acupuncture points after the patient puts on the therapy clothes in such a manner that treatment effects are provided. The self-heating tourmaline slice is made of nano functional ceramics powder and special thermoinduction materials which instantly generates a heat up to 40° C. with transfer catalyst after activated by body temperature. Under amplification of the heat, far-infrared negative ions emitted can go deep into skins, promote blood circulation, activate cells, promote the metabolism, regulate nervous system, activate incretion, relieve pain and cure cold. Therefore, the far-infrared negative ions have an significant effect on arthritis and joint pain. The self-heating tourmaline slices will automatically generate the heat for stimulating the acupuncture points in such a manner that a better treatment or care effect is provided.

When the self-heating tourmaline slices are replaced by the metal clamps, heat up to 43° C. with an obvious treatment effect will be generated by magnetic induction with the dynamic magnetic fields provided by the upper and lower magnetic heads. When a higher temperature is needed for treatment, heat can be generated by electromagnetic induction (which has a same principle with an electromagnetic stove). That is to say, the high-frequency alternating current is provided by the high-frequency power supplier, and the high-frequency alternating current is added on a helical high-frequency heating induction coil for generating a high-frequency alternating magnetic field, whose magnetic lines act on the metal clamps. A strong eddy current is generated in the metal clamps because of the electromagnetic induction. The eddy current transforms electrical energy to thermal energy when overcoming inner resistance. Joule heat generated will be a heat source and a calorific value can be controlled by adjusting a power of the high-frequency power supplier. That is to say, the calorific value of the metal clamps can be controlled within 40~60° C. by medical staffs according to a condition of a patient in such a manner that treatment methods are stricter and more effective.

D) The therapy clothes are in the sleeping bag form or the split form. The sleeping bag form is suitable for caring the whole body, wherein the sleeping bag form can coving the whole body for the better treatment effects. The therapy clothes in the split form comprise:
the head cover with the ear, nose and mouth openings;
the body cover; and
the limb covers;
wherein the waterproof sealing bars are provided on the openings of the head, body and limb covers, and the head, body and limb covers are respectively connected to the physiotherapy liquid collection tank.

During the treatment, only the diseased portions covered by the therapy clothes, which is convenient. Local or systemic treatments can be provided by the medical staff according to the condition of the patient, which is more accurate and reasonable.

E) The emulsion rollers are provided on the treatment bed. The emulsion rollers are mounted below the neck bend, the waist bend, the leg bends and the foot bends of the therapy clothes according to ergonomics, which can effectively support and correct curves of the body as well as recover body skeleton for stretching muscles and promoting the blood circulation. The emulsion rollers are respectively connected to the micro motors, and the micro motors drive the emulsion rollers to rotate individually. Under a combined magnetic field, the bends are further cared in such a manner that more massages are provided on the diseased portions and heath is restored more quickly.

F) The tourmaline slices or the halite slices are provided on the top surface of the treatment bed. And the radial protrusions are provided on the emulsion roller. The top of the radial protrusion is inlaid with the halite grain. The metal heating mandrel is mounted in the emulsion roller. After the high-frequency power supplier provides the high-frequency alternating current for the high-frequency heating induction coil, the metal heating mandrels generate heat in such a manner that the halite can cure code. For patients with code, the therapy clothes are not needed. Each patient has an individual set of the halite slices which is dried every day. The halite slices are replaced once every course for better effect.

G) The basic liquid of the auxiliary physiotherapy liquid comprises:
glycerol; and
olive oil.

The traditional Chinese medicine additive can be added in the basic liquid in a powder form. The basic liquid surrounds the body or the diseased portion, and carries the traditional Chinese medicine additive into the circulatory system because the glycerol and the olive oil have high solubility and can be absorbed easily by the body. Different traditional Chinese medicines can be added into the basic liquid according to the condition of the patient. For example, *madeiravine bulbil* physiotherapy liquid can be added for treating diabetes, hypertension and hyperlipidemia; *taxus chinensis* physiotherapy liquid can be added for treating malignant tumour; wrinkled giant hyssop physiotherapy liquid can be added for treating rheumatalgia; and *sedum sarmentosum* can be added for relieving fatigue, which are convenient and accurate. Different medicine plans and course durations can be provided by the medical staffs for different periods according to the condition of the patient. The heater is provided in the physiotherapy liquid collection tank and as well as the temperature controller for accurately controlling a temperature of the physiotherapy liquid and taking full advantage of the treatment effect.

H) The present invention is a perfect combination of Chinese and Western medicine: the computer control system coordinates various components. The rotation speed of the magnetic head, height of the lifting arm and the rotation speed of the emulsion roller can be accurately preselected according to the condition of the patient. And the treatment is more accurate and reasonable. By applying the magnetic principle of the Western medicine on the human body, anti-cancer and blood-thinning effects can be achieved. With high-speed metabolism, utilizing the traditional Chinese medicine can accelerate a recovery process. And the patient has no pain during the treatment and is more cooperative, and the treatment can be extremely effective. Therefore, the present invention is very suitable for popularization in the medicine field.

These and other objectives, features, and advantages of the present invention will become apparent from the following detailed description, the accompanying drawings, and the appended claims.

Figure 1:
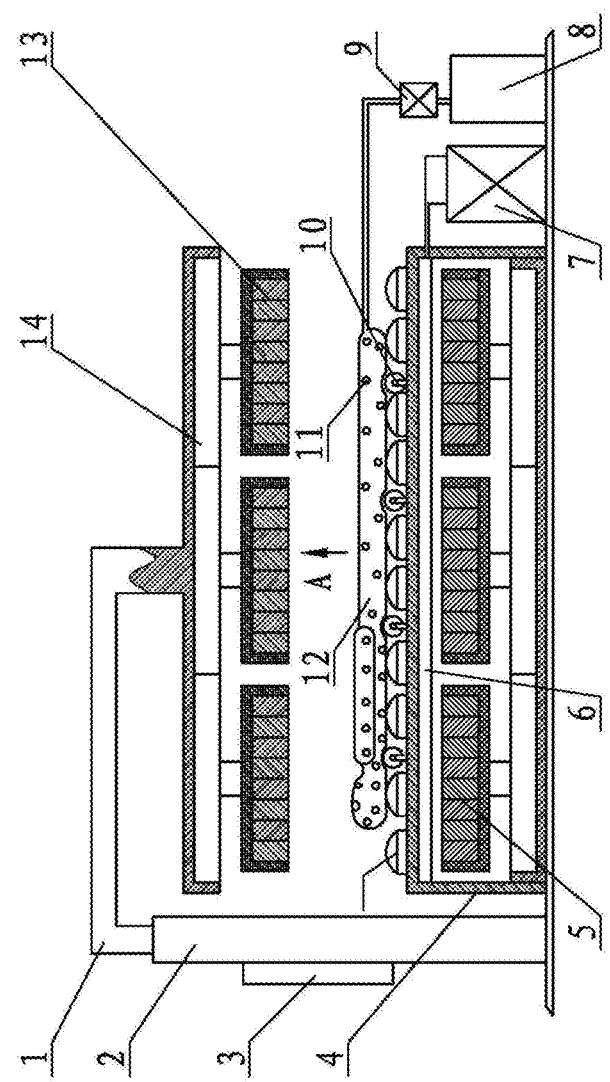
FIG. 1 is a sketch view of a preferred embodiment 1 according the present invention.

Reference numbers of elements: 1—lifting arm, 2—upright post, 3—computer control system, 4—treatment bed, 5—lower magnetic head, 6—high-frequency heating induction coil layer, 7—high-frequency power supplier, 8—physiotherapy liquid collection tank, 9—circulation pump, 10—emulsion roller, 11—self-heating tourmaline slice, 12—therapy clothes, 13—upper magnetic head, 14—upper magnetic head holder, 15—permanent magnetic block, 16—cambered salient point, 17—tourmaline slice, 18—high-frequency heating induction coil, 19—radial protrusion, 20—metal heating mandrel, 21—halite grain, 22—upper magnetic head, 23—metal clamp, 24—helite slice, 25—lower magnetic head.

DETAILED DESCRIPTION OF THE PREFERRED EMBODIMENT

Referring to the drawings, the present invention is further illustrated.

Preferred Embodiment 1

Figure 2:
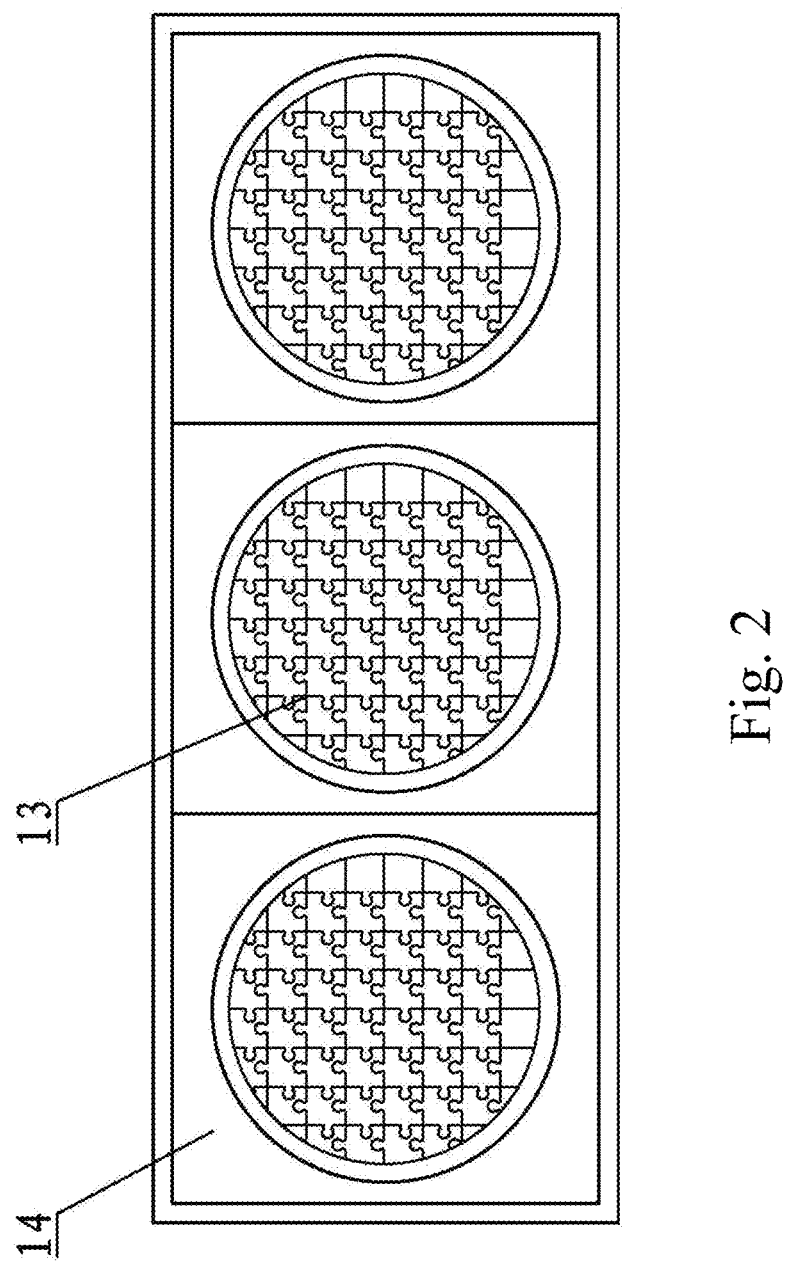
FIG. 2 is an A-direction sketch view of the FIG. 1 according to the present invention.
Figure 13:
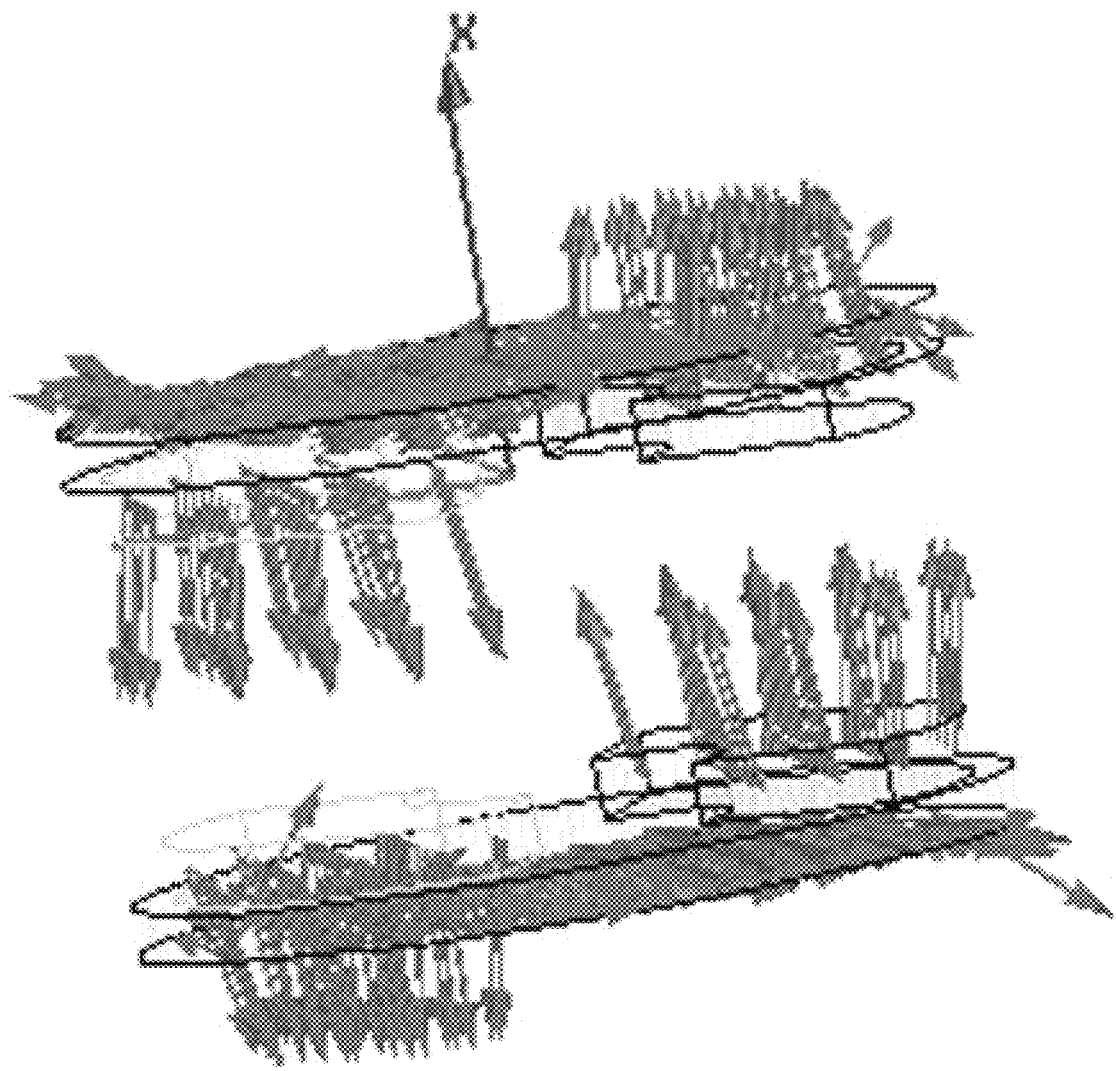
FIG. 13 is a distribution view of magnetic lines between an upper magnetic head and a lower magnetic head according to the present invention.
Figure 14:
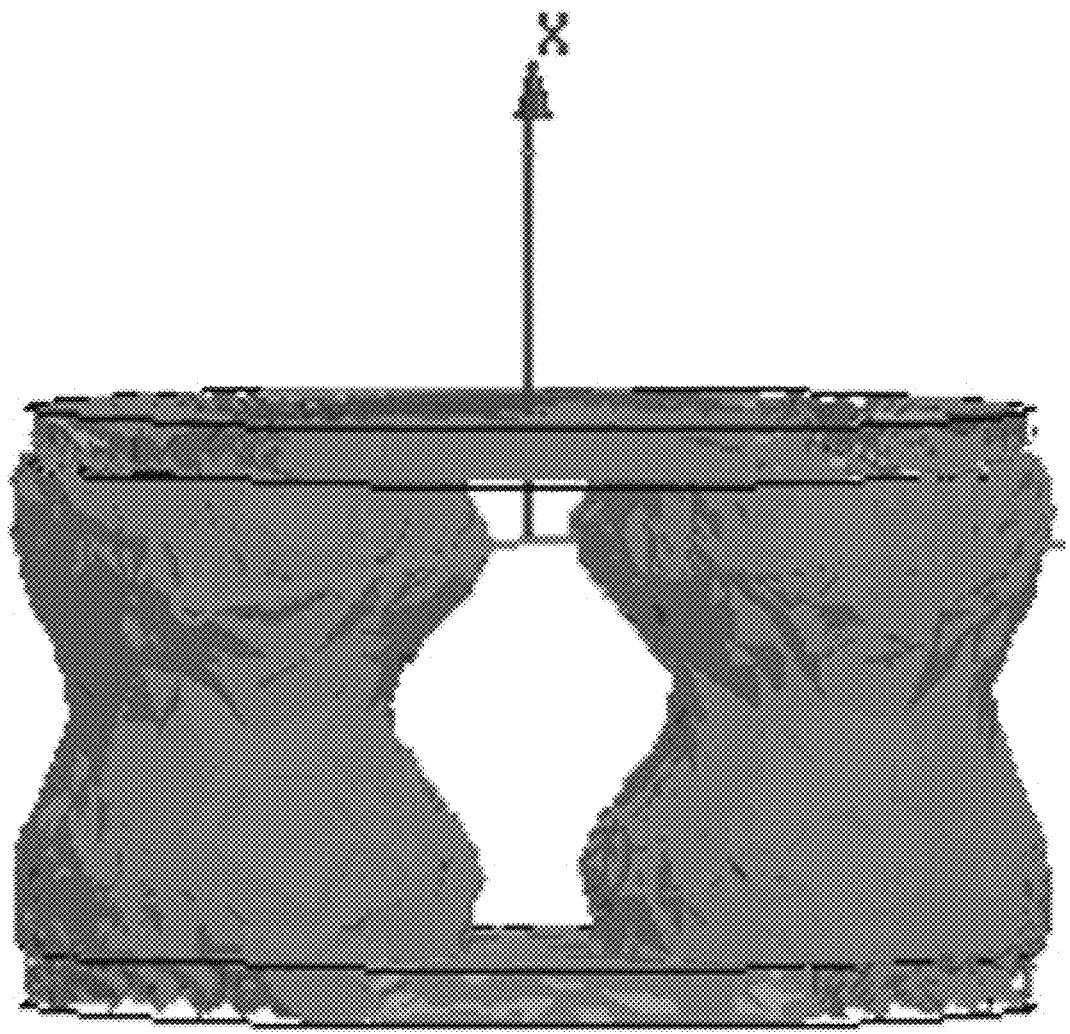
FIG. 14 is a distribution view of magnetic strength between an upper magnetic head and a lower magnetic head according to the present invention.

Referring to FIG. 1 of the drawings, an electromagnetic therapy apparatus is illustrated, wherein a lifting arm 1 is inserted in an upright post 2 and is driven to go up and down by a lifter, wherein the lifter can be a lifting motor or an air cylinder. The upper magnetic head holder 14 is connected to the lifting arm 1. Three upper magnetic heads 13 are mounted on the upper magnetic head holder 14 through bearings. A treatment bed 4 is provided below the upper magnetic heads 13. Three lower magnetic heads 5 and rotary power suppliers thereof (the rotary power supplier is a micro motor, which is not shown in the drawings) are mounted on the treatment bed 4 as shown in FIG. 2. Each of the lower magnetic heads 5 is driven by the rotary power supplier to rotate individually. Vertical mounting positions of the upper magnetic heads 13 are respectively corresponding and opposite to vertical mounting positions of the lower magnetic heads 5. The rotary power suppliers drive the lower magnetic heads 5 to rotate in such a manner that the lower magnetic heads 5 drive the upper magnetic heads 13 to rotate by magnetic force coupling. Distribution views of magnetic lines and magnetic strength between the upper magnetic head 13 and the lower magnetic head 5 are shown in FIG. 13 and FIG. 14.

Figure 15:
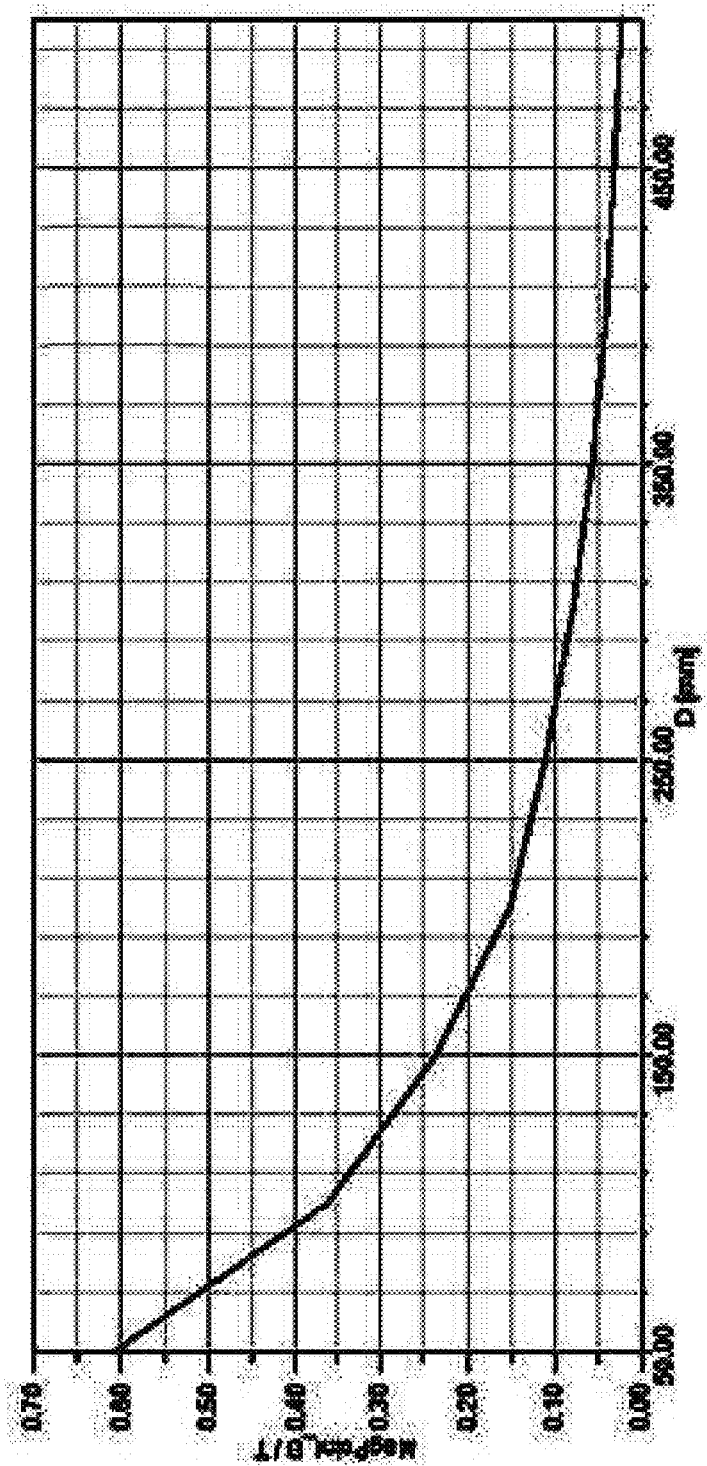
FIG. 15 is a curve of magnetic strength of a point between an upper magnetic head and a lower magnetic head according to a distance therebetween according to the present invention.

Static magnetic field strength of the upper magnetic heads 13 and the lower magnetic heads 5 is 3000 Gs. A rotation speed of the lower magnetic head 5 is 50 rpm. A distance between the upper magnetic head 13 and the lower magnetic head 5 is 200 mm. Referring to FIG. 15, a curve view of the magnetic strength of a point between the upper magnetic head 13 and the lower magnetic head 5 according to the distance therebetween according to the present invention is illustrated. It can be seen that the longer the distance is, the weaker the magnetic strength will be. The upper magnetic heads 13 and the lower magnetic heads 5 are disc-shaped. And a ratio of a center distance between the magnetic heads and a diameter of the magnetic head is 1.2:1.

Figure 3:
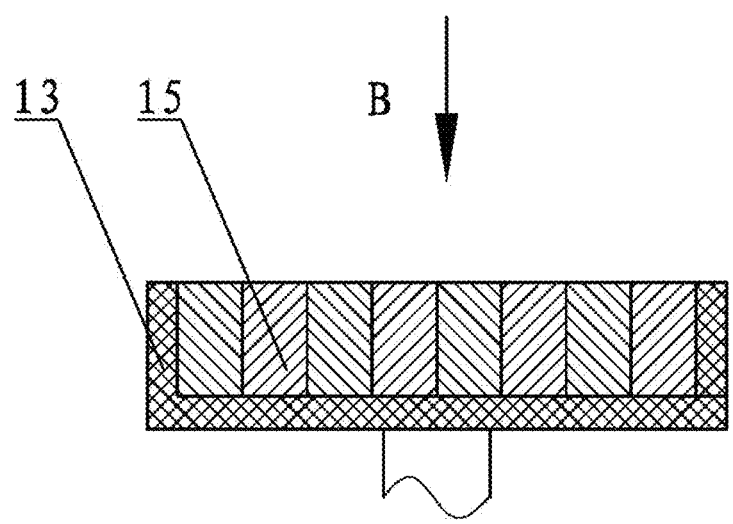
FIG. 3 is a sectional view of an upper magnetic head according to the present invention.
Figure 4:
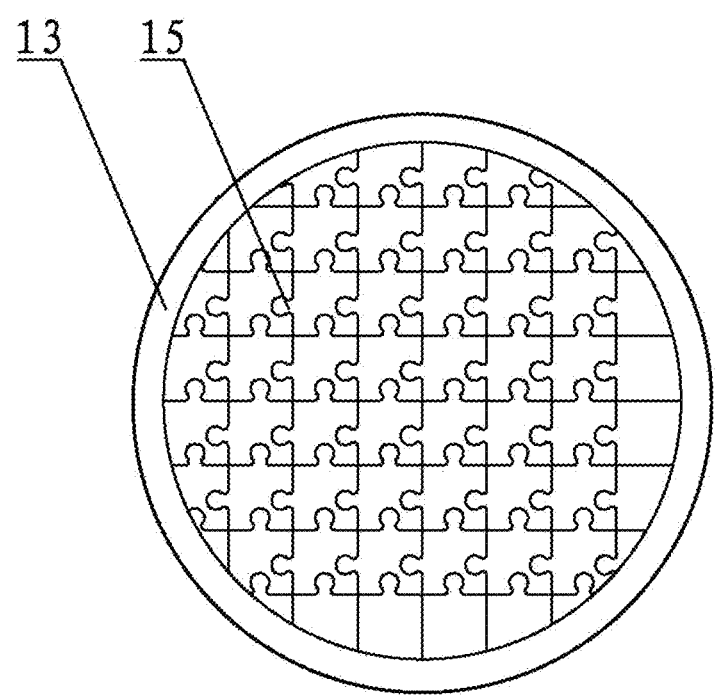
FIG. 4 is a B-direction sketch view of the FIG. 3 according to the present invention.
Figure 16:
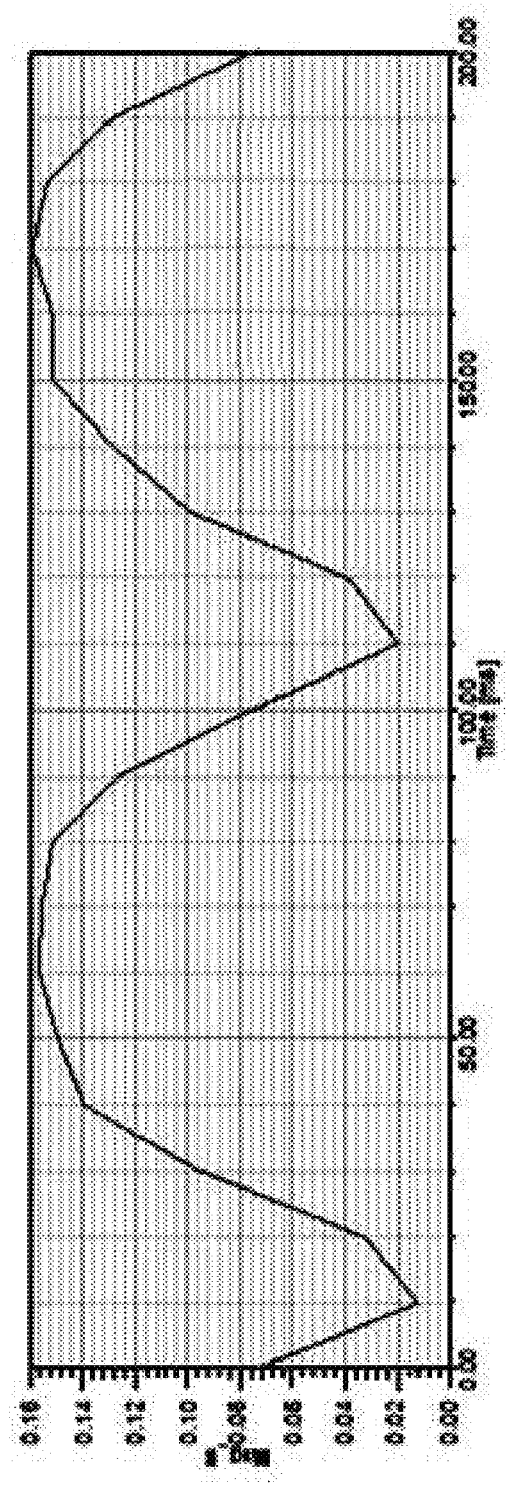
FIG. 16 is a curve of magnetic strength of a point between an upper magnetic head and a lower magnetic head according to time according to the present invention.

Referring to FIG. 3 and FIG. 4 of the drawings, the upper magnetic heads 13 and the lower magnetic heads 5 are permanent magnetic heads, a plurality of permanent magnetic blocks 15 are spliced for forming the upper magnetic heads 13 and the lower magnetic heads 5, and gaps exist between the permanent magnetic blocks 15. When the magnetic heads rotates, because of a phase difference (which means the upper magnetic heads 13 and the lower magnetic heads 5 do not rotate synchronously), the magnetic fields of the upper magnetic heads 13 and the lower magnetic heads 5 change alternatively for generating pulse with treatment effects. Referring to FIG. 16 of the drawings, a curve of the magnetic strength of a point between the upper magnetic heads 13 and the lower magnetic heads 5 according to time is in a pulse form for providing therapeutic interventions to human bodies.

Arrangement of the magnetic blocks 15 is calculated according to waveform, amplitude and frequency of a dynamic magnetic field. A calculation result is compared with a standard waveform. If the calculation result is marching with the standard waveform, the magnetic blocks 15 can be mounted. Parameters selected of the dynamic magnetic field (such as waveform, induction electromotive force, frequency, treatment duration and treatment cycle) can enhance bioelectric current of the human body as well as promote oxygen carrying capacity, speed and breadth of red blood cells for promoting metabolism as well as curing and recovering from chronic diseases such as malignant tumor.

The three pairs of the upper magnetic heads 13 and the lower magnetic heads 5 are corresponding to chest, abdomen and legs. The upper magnetic heads 13 and the lower magnetic heads 5 can rotate according to diseased portions for curing and recovering.

Therapy clothes 12 are provided on the treatment bed 4. The therapy clothes 12 are in a sleep bag form in such a manner that the therapy clothes 12 can be put on easily. And waterproof sealing bars are provided on ear, nose and mouth openings of the therapy clothes 12. After putting on the therapy clothes 12, the patient seals the openings by pressing the waterproof sealing bars in such a manner that physiotherapy liquid is preserved from leakage.

Figure 5:
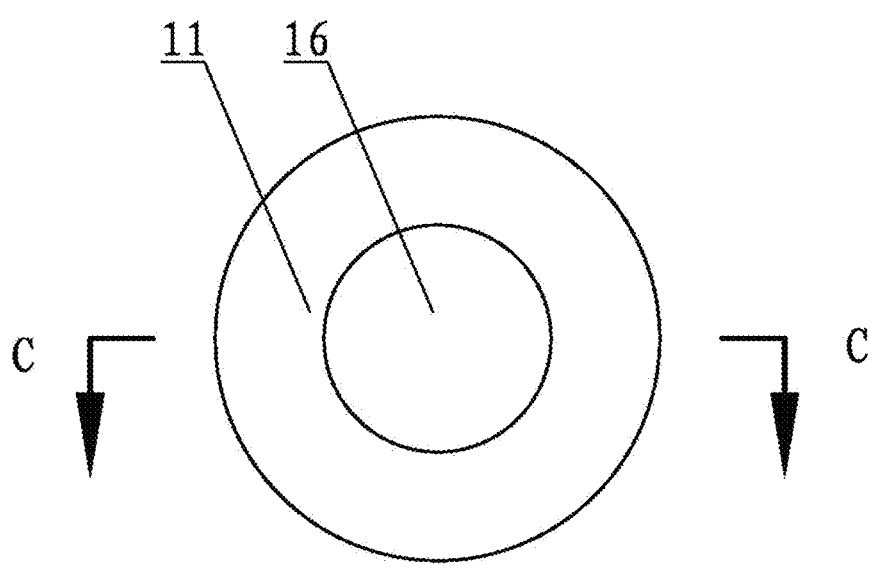
FIG. 5 is a sketch view of a metal clamp (or a self-heating tourmaline slice) according to the present invention.
Figure 6:
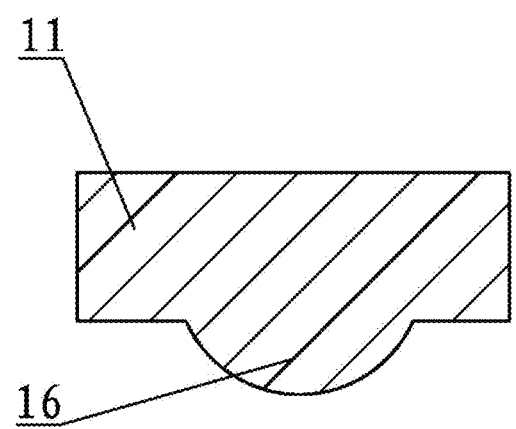
FIG. 6 is a C-C sectional view of the FIG. 5 according to the present invention.

Referring to FIGS. 1, 5 and 6 of the drawings, padding is provided in the therapy clothes 12. And self-heating tourmaline slices 11 are mounted between the therapy clothes 12 and the padding according to acupuncture points. Cambered salient points 16 are provided on the self-heating tourmaline slices 11. The self-heating tourmaline slices 11 can stimulate the acupuncture points after contacting with skins and water for better treatment effects.

The therapy clothes 12 are connected to a physiotherapy liquid collection tank 8 through a circulation pump 9. The physiotherapy liquid is stored in the physiotherapy liquid collection tank 8. With the circulation pump 9, the physiotherapy liquid forms a uniform layered structure for covering the whole body and can flow circularly. When blood circulation and metabolism are accelerated by the magnetic field, the physiotherapy liquid can be absorbed easily and effects thereof can directly affect diseased portions. A heater is provided in the physiotherapy liquid collection tank 8 and is connected to a temperature controller. The physiotherapy liquid is heated to a suitable temperature of 40~60° C. before being injected into the therapy clothes 12 by the circulation pump 9 in such a manner that treatment effects are more sufficient.

The physiotherapy liquid comprises:
basic liquid; and
a traditional Chinese medicine additive;
wherein the basic liquid comprises:
glycerol; and
olive oil;
wherein a ratio of the glycerol and the olive oil is 1:1.

Different traditional Chinese medicine can be added according to diseases of patients. The traditional Chinese medicine additive is selected from the group consisting of Chinese *angelica, safflower, Notopterygium, rattan Panax, yew, Agastache* and *sarmentosum*; a ratio of the basic liquid and the traditional Chinese medicine additive is 10:1.

Figure 7:
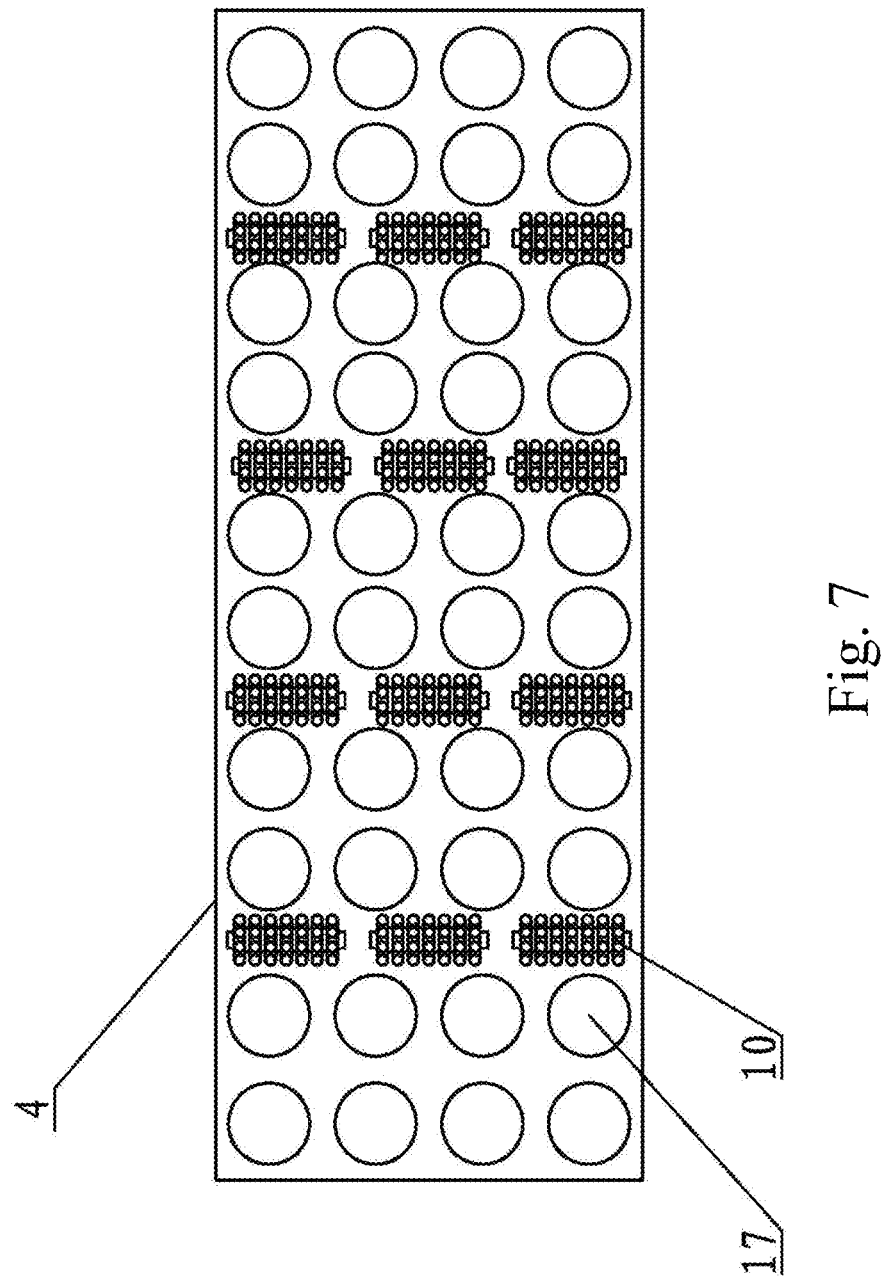
FIG. 7 is a sketch view of a top surface of a treatment bed according to the present invention.
Figure 8:
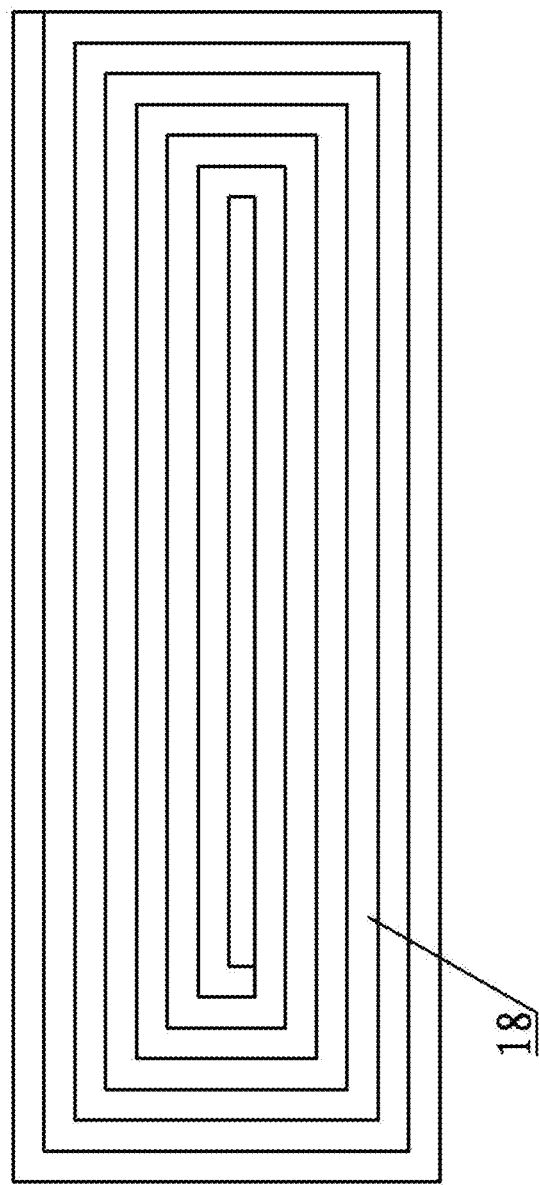
FIG. 8 is a sketch view of a high-frequency heating induction coil according to the present invention.
Figure 9:
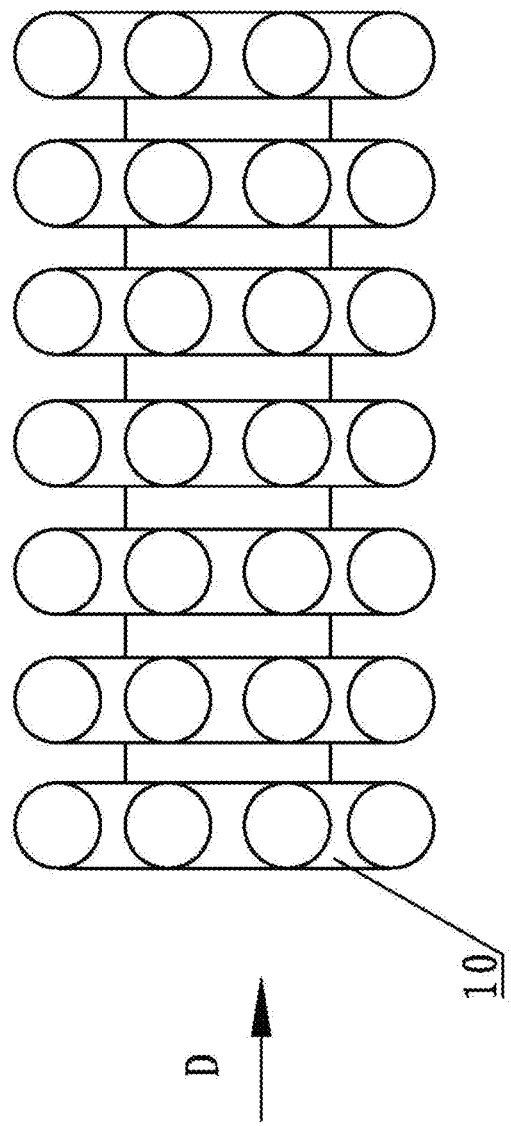
FIG. 9 is a sketch view of an emulsion roller according to the present invention.
Figure 10:
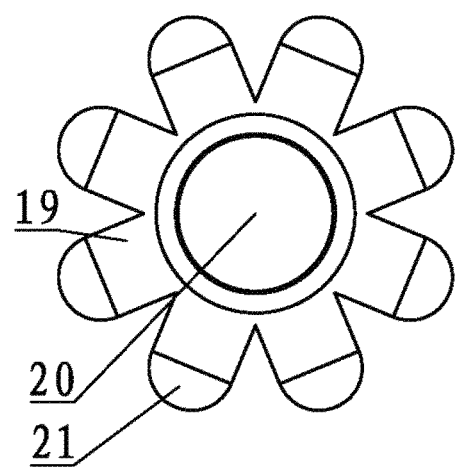
FIG. 10 is a D-direction sketch view of the FIG. 9 according to the present invention.

Referring to FIG. 7 of the drawings, tourmaline slices are provided on a top surface of the treatment bed 4. Emulsion rollers 10 are also provided on the treatment bed 4. The emulsion rollers 10 are mounted below a neck bend, a waist bend, leg bends and foot bends of the therapy clothes 12. The emulsion rollers 10 are respectively connected to micro motors, and the micro motors drive the emulsion rollers 10 to rotate individually for providing massages. Referring to FIGS. 9 and 10 of the drawings, radial protrusions 19 are provided on the emulsion roller 10. A top of the radial protrusion 19 is inlaid with a halite grain 21. A metal heating mandrel 20 is mounted in the emulsion roller 10. A high-frequency heating induction coil layer 6 in provided in the treatment bed 4, and a high-frequency heating induction coil 18 is provided thereon. Referring to FIG. 8 of the drawings, after a high-frequency power supplier 7 provides a high-frequency alternating current for the high-frequency heating induction coil 18, the metal heating mandrels 20 generate heat in such a manner that the halite can cure code. For patients with code, the therapy clothes 14 are not needed and the patients can lie on the treatment bed 4 directly. Each patient has an individual set of mattresses which is dried every day. The halite slices are replaced once every course for better effects.

While working, a computer control system 3 is connected to and controls the rotary power suppliers, the circulation pump 9, the micro motors, the lifter and the temperature controller. A rotation speed of the magnetic head, height of the lifting arm 1, a rotation speed of the emulsion roller 10 and a temperature of the physiotherapy liquid can be accurately preselected according to the condition of the patient. And the treatment is more accurate and reasonable. Furthermore, additives in the therapy clothes 12 can be changed according to the patient, or the patient can lie on the treatment bed 4 directly. Gyromagnetic treatment, which is flexible, convenient, easy to operation and painless, is provided by the lower magnetic heads 5 the upper magnetic heads 13.

Preferred Embodiment 2

Figure 11:
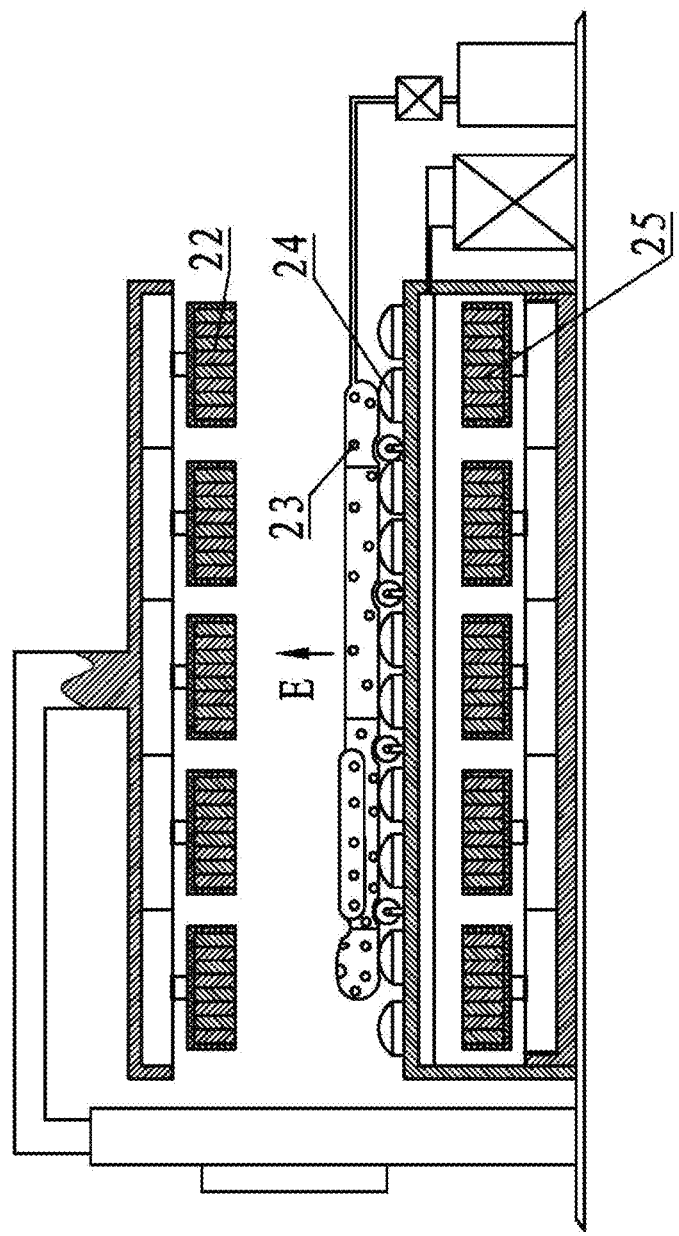
FIG. 11 is a sketch view of a preferred embodiment 2 according to the present invention.
Figure 12:
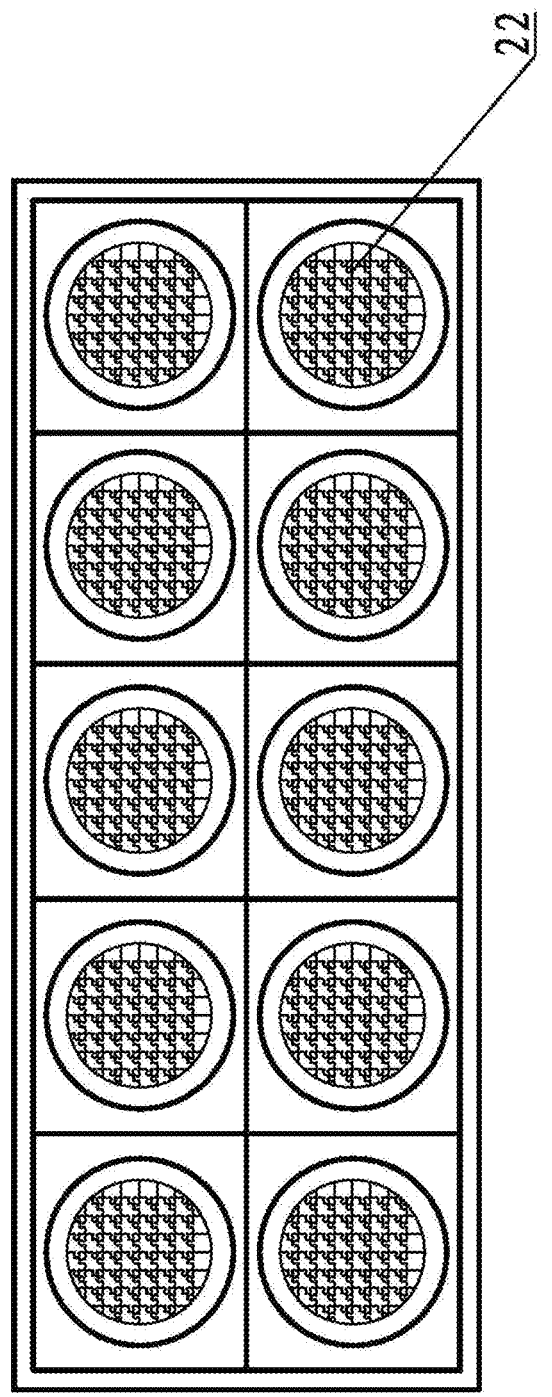
FIG. 12 is an E-direction sketch view of the FIG. 11 according to the present invention.

Referring to FIG. 11 and FIG. 12 of the drawings, the lower magnetic heads 25 and the upper magnetic heads 22 are electromagnetic heads and a total amount is 10. A cooling device is provided around the electromagnetic heads. An induction electromotive force of an electromagnetic wave generated by the electromagnetic heads is 500 mv with a frequency of 8 Hz. Positions of the upper magnetic heads 22 are respectively corresponding and opposite to positions of the lower magnetic heads 25. The rotary power suppliers drive the lower magnetic heads 25 to rotate for driving the upper magnetic heads 22 to rotate by magnetic force coupling. Static magnetic field strength of the lower magnetic heads 25 the upper magnetic heads 22 is 8500 Gs. A rotation speed of the lower magnetic heads 25 is 600 rpm. With the foregoing structure, not only a sufficient gyromagnetic treatment effect is provided, but also the lower magnetic heads 25 the upper magnetic heads 22 in different positions can be activated alternatively in such a manner that a blood viscous region of a patient spread to tributaries for relieving blood viscosity and thrombus disease.

The therapy clothes 12 in the split form comprise:
a head cover with the ear, nose and mouth openings;
a body cover; and
limb covers;
wherein the waterproof sealing bars are provided on the openings of the head, body and limb covers, and the head, body and limb covers are respectively connected to the physiotherapy liquid collection tank 8.

Local or systemic treatments can be provided by the medical staff according to the condition of the patient, which is more accurate and reasonable.

The tourmaline slices on the treatment bed 4 is replaced by halite slices 24. The self-heating tourmaline slices 11 in the therapy clothes 12 are replaced by metal clamps 23. The metal clamps have a same structure as the self-heating tourmaline slices 11 and are also provided in the therapy clothes 12 according the acupuncture points. The cambered salient points 16 are also provided on the metal clamps 23. The high-frequency heating induction coil layer 6 in provided in the treatment bed 4, and the high-frequency heating induction coil 18 is provided thereon. Referring to the FIG. 8 of the drawings, after the high-frequency alternating current is provided by the high-frequency power supplier 7, heat can be generated by electromagnetic induction (which has a same principle with an electromagnetic stove). The high-frequency alternating current is added on a helical high-frequency heating induction coil 18 for generating a high-frequency alternating magnetic field, whose magnetic lines act on the metal clamps 23. A strong eddy current is generated in the metal clamps 23 because of the electromagnetic induction. The eddy current transforms electrical energy to thermal energy when overcoming inner resistance of the metal clamps 23. Joule heat generated will be a heat source and a calorific value can be controlled by adjusting a power of the high-frequency power supplier 7. That is to say, the calorific value of the metal clamps 23 can be controlled within 40~60° C. according to a condition of a patient in such a manner that treatment methods are stricter and more effective.

The ratio of the glycerol and the olive oil is 1:2. The ratio of the basic liquid and the traditional Chinese medicine additive is 10:1.2.

The other structures and methods of the preferred embodiment 2 are the same as the preferred embodiment 1 and will not be recited again.

Preferred Embodiment 3

Referring to the FIG. 11 and the FIG. 12 of the drawings, the lower magnetic heads 25 the upper magnetic heads 22 are the electromagnetic heads and the total amount is 10. The induction electromotive force of an electromagnetic wave generated by the electromagnetic heads is 1000 mv with a frequency of 20 Hz. The static magnetic field strength of the lower magnetic heads 25 the upper magnetic heads 22 is 8500 Gs. A rotation speed of the lower magnetic heads 25 is 430 rpm. A distance between the lower magnetic heads 25 the upper magnetic heads 22 is 350 mm.

The ratio of the glycerol and the olive oil is 1:3. The ratio of the basic liquid and the traditional Chinese medicine additive is 10:1.5.

The other structures and methods of the preferred embodiment 3 are the same as the preferred embodiment 1 and will not be recited again.

Preferred Embodiment 4

The lower magnetic heads 25 the upper magnetic heads 22 are the electromagnetic heads and the total amount is 10. The induction electromotive force of an electromagnetic wave generated by the electromagnetic heads is 2000 mv with a frequency of 30 Hz. The static magnetic field strength of the lower magnetic heads 25 the upper magnetic heads 22 is 6500 Gs. A rotation speed of the lower magnetic heads 25 is 560 rpm. A distance between the lower magnetic heads 25 the upper magnetic heads 22 is 400 mm.

The other structures and methods of the preferred embodiment 4 are the same as the preferred embodiment 1 and will not be recited again.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An electromagnetic therapy apparatus comprising:
a frame;
a treatment bed, wherein a plurality of emulsion rollers are provided on said treatment bed;
a plurality of upper magnetic heads mounted on said frame by bearings;
a plurality of lower magnetic heads mounted in said treatment bed, where each of said lower magnetic heads is connected to a rotary power supplier and driven to rotate individually by said rotary power supplier;
vertical mounting positions of said upper magnetic heads are respectively corresponding and opposite vertical mounting positions of said lower magnetic heads;
said rotary power supplier drives said lower magnetic heads to rotate, then said lower magnetic heads drive said upper magnetic heads to rotate by magnetic force coupling; and
therapy clothes provided on said treatment bed, wherein said emulsion rollers are mounted on said treatment bed for heating said therapy clothes;
waterproof sealing bars are provided on openings of said therapy clothes;
said therapy clothes are connected to a physiotherapy liquid collection tank through a circulation pump;
padding is provided in said therapy clothes, and a plurality of self-heating tourmaline slices or metal clamps are mounted between said therapy clothes and said padding.

2. The electromagnetic therapy apparatus, as recited in claim 1, wherein a high-frequency heating induction coil connected to a high-frequency power supplier is mounted in said treatment bed.

3. The electromagnetic therapy apparatus, as recited in claim 2, wherein said upper and lower magnetic heads are electromagnetic heads, a cooling device is provided around said electromagnetic heads; an induction electromotive force of an electromagnetic wave generated by said electromagnetic heads is 500-1000 mv with a frequency of 8-20 Hz; said upper and lower magnetic heads comprise a plurality of electromagnetic blocks which are spliced for forming said upper and lower magnetic heads, and gaps exist between said electromagnetic blocks.

4. The electromagnetic therapy apparatus, as recited in claim 3, wherein said upper and lower magnetic heads have a static magnetic field strength of 5000-8500 Gs.

5. The electromagnetic therapy apparatus recited in claim 4, wherein a rotation speed of said lower magnetic heads is 50-600 rpm, and a distance between said upper and lower magnetic heads is: 200-400 mm.

6. The electromagnetic therapy apparatus, as recited in claim 5, wherein said upper and lower magnetic heads are disc-shaped, and a ratio of a center distance between said upper and lower magnetic heads and a diameter of said magnetic head is 1.2:1.

7. The electromagnetic therapy apparatus, as recited in claim 6, wherein said self-heating tourmaline slices or metal clamps are provided between said therapy clothes and said padding according to acupuncture points, and cambered salient points are provided on said self-heating tourmaline slices or metal clamps.

8. The electromagnetic therapy apparatus, as recited in claim 7, wherein said therapy clothes are in a sleeping bag form or a split form.

9. The electromagnetic therapy apparatus, as recited in claim 8, wherein said therapy clothes in said split form comprise:
a head cover with ear, nose and mouth openings;
a body cover; and
limb covers;
wherein the waterproof sealing bars are provided on said openings of said head, body and limb covers, and said head, body and limb covers are respectively connected to said physiotherapy liquid collection tank.

10. The electromagnetic therapy apparatus, as recited in claim 9, wherein a plurality of tourmaline slices or halite slices are provided on a top surface of said treatment bed.

11. The electromagnetic therapy apparatus, as recited in claim 10, wherein said emulsion rollers are mounted below a neck bend, a waist bend, leg bends and/or foot bends of said therapy clothes; said emulsion rollers are respectively connected to micro motors, and said micro motors drive said emulsion rollers to rotate individually.

12. The electromagnetic therapy apparatus, as recited in claim 11, wherein radial protrusions are provided on said emulsion rollers, a top of each of said radial protrusions is inlaid with a halite grain; a metal heating mandrel is mounted in said emulsion roller; after said high-frequency power supplier provides a high-frequency alternating current for said high-frequency heating induction coil, said metal clamps and said metal heating mandrel generate heat at the same time.

13. The electromagnetic therapy apparatus, as recited in claim 12, wherein said frame comprises:
an upright post;
a lifting arm;
a lifter; and
a upper magnetic head holder;
wherein said lifting arm is inserted in said upright post and is driven to go up and down by said lifter; said upper magnetic head holder is connected to said lifting arm, said upper magnetic heads are mounted on said upper magnetic head holder.

14. The electromagnetic therapy apparatus, as recited in claim 13, wherein a heater is provided in said physiotherapy liquid collection tank and is connected to a temperature controller.

15. The electromagnetic therapy apparatus, as recited in claim 14, further comprising: a computer control system, wherein said computer control system is connected to and controls said rotary power suppliers, said circulation pump, said micro motors, said lifter and said temperature controller.

16. The electromagnetic therapy apparatus, as recited in claim 2, wherein said upper and lower magnetic heads are permanent magnetic heads; said upper and lower magnetic heads comprise a plurality of permanent magnetic blocks which are spliced for forming said upper and lower magnetic heads, and gaps exist between said permanent magnetic blocks.

17. The electromagnetic therapy apparatus, as recited in claim 16, wherein said upper and lower magnetic heads have a static magnetic field strength of 5000-8500 Gs.

* * * * *